United States Patent [19]

Minekane

[11] Patent Number: 4,685,801
[45] Date of Patent: Aug. 11, 1987

[54] APPARATUS FOR ABSORPTIOMETRIC ANALYSIS

[75] Inventor: Tomiharu Minekane, Ootawara, Japan

[73] Assignee: Tokyo Shibaura Denki Kabushiki Kaisha, Kawasaki, Japan

[21] Appl. No.: 814,169

[22] Filed: Dec. 23, 1985

Related U.S. Application Data

[63] Continuation of Ser. No. 541,658, Oct. 13, 1983, abandoned.

[30] Foreign Application Priority Data

Oct. 15, 1982 [JP] Japan ................................. 57-179753

[51] Int. Cl.[4] ............................ G01J 3/08; G01J 3/42
[52] U.S. Cl. .................................... 356/328; 422/63; 422/68; 436/47
[58] Field of Search ........ 356/326, 328, 319, 409–411, 356/432, 433, 436, 440; 436/34, 43, 47; 422/63–65, 68

[56] References Cited

U.S. PATENT DOCUMENTS 3,697,185 10/1972 Kassel et al. ...................... 356/410
4,063,817 12/1977 Shimamura et al. .
4,411,519 10/1983 Tagami .................... 356/45
4,487,504 12/1984 Goldsmith ...................... 356/323

FOREIGN PATENT DOCUMENTS 2451769 5/1975 Fed. Rep. of Germany .
2408543 8/1975 Fed. Rep. of Germany .
2469713 5/1981 France .
151084 11/1979 Japan ................................. 356/328
72108 4/1983 Japan ............................... 350/96.15

Primary Examiner—F. L. Evans
Attorney, Agent, or Firm—Cushman, Darby & Cushman

[57] ABSTRACT

The beam from a xenon flashed lamp driven by a pulse drive system is guided through 12 illumination beam guiding optical fibers, to illuminate a reaction liquid contained in 12 reaction cuvettes (with every 4 reaction cuvettes being located at each of 3 different measuring stations). The beam transmitted through the reaction liquid is so led as to be incident on 12 transmitted beam guiding optical fibers. The beam emission ends of the transmitted beam guiding optical fibers are inserted into a support member at positions thereof which fall on a circle. The rotor is rotated in conjunction with a shaft. A pair of reflecting mirrors are secured to the rotor and shaft, respectively. The beams emitted from the transmitted beam guiding optical fibers are independently and consecutively led along the same optical path, to a pair of slit members disposed on the side of the rotor opposite the support member, while the rotor completes one rotation. The beam passed through the slit members is diffracted by a diffraction grating, and diffracted beams are detected by a photodetector array.

7 Claims, 4 Drawing Figures

APPARATUS FOR ABSORPTIOMETRIC ANALYSIS

This is a continuation of application Ser. No. 541,658, filed Oct. 13, 1983, which was abandoned upon the filing hereof.

BACKGROUND OF THE INVENTION

This invention relates to an apparatus for absorptiometric analysis in the field of automatic chemical analysis apparatus and, more particularly, to an absorbance measuring apparatus which can quickly effect absorbance measurement processes on a number of samples for a plurality of measurement items.

FIG. 1 shows a conventional absorbance measuring apparatus. A beam emitted from a light source 10 is incident on a bundle of optical fibers 12 and is led through these optical fibers 12 to reaction tubes 20 for a plurality of channels located in, for instance, three measuring stations, i.e., first to third measuring stations 14, 16 and 18. In the illustrated example, each measuring station has four channels, though a reaction tube for only one of these channels is shown for each measuring station. Reflecting mirrors 22 are each disposed on the side of each reaction tube 20 opposite the beam emission end of the corresponding optical fiber. The beam emitted from each optical fiber 12 is transmitted through a reaction liquid contained in each reaction cuvette 20 and is then reflected by each reflecting mirror 22. Beams reflected from the individual reflecting mirrors 22 are incident on two-wavelength spectrometers 24, 26 and 28, respectively. Each of the two-wavelength spectrometers includes a beam splitter 30 and spectrometers 32 and 34. The beam splitter 30 splits the incident beam into two light beams which are led to the pair of spectrometers 32, 34. The spectrometers 32, 34 each include a filter and a photo-detector, and can measure the intensity of transmitted light of particular wavelengths.

A sample serum, for example, is distributed to the reaction tubes 20 for four channels, and different reagents for the respective channels are poured into the sample serum in the individual reaction tubes 20. The reaction tubes 20, each of which contains the reaction liquid, i.e., the mixture of sample serum and reagent, are brought to the successive first to third measuring stations 14, 16 and 18, and the intensity of the transmitted beam is measured for two different wavelengths at each of the measuring stations. Changes in the absorbance (i.e., the reaction degree) of the reaction liquid, over time, can thus be measured, whereby an examination can be conducted for four different channels of items (such as GOT and GPT) in the respective samples.

In this absorbance measuring apparatus, two-wavelength spectrometers 24, 26, 28 must be provided for the individual channels at the respective measuring stations. Therefore, the cost and size of the apparatus are increased to that extent. Further, since changes in the absorbance of each reaction liquid, over time, are measured by different two-wavelength spectrometers 24, 26, 28, the results of examination are subject to error, due to variations in the light-electricity conversion characteristics among the individual two-wavelength spectrometers 24, 26, 28. This is a serious drawback; and, where examination is done by measuring the enzyme activities of GOT or GPT, which can undergo fewer absorbance changes, the drawback is so serious that the examination becomes impossible. Moreover, the optical fibers 12 have a low filling factor, so that a high output halogen lamp which continuously emits light is used as the light source 10. A beam of such a high energy level, however, would cause decomposition of a reaction liquid obtained from, for instance, the serum of a jaundice patient, thus disabling accurate examination.

FIG. 2 shows a different conventional absorbance measuring apparatus. In this case, a plurality of reaction cuvettes 46 are disposed along a circle for each of the different channels 36, 38, .... The reaction cuvettes 46 for each channel are moved about the center of the circle. When each reaction cuvette 46 is at an absorbance measuring position, a beam emitted from a light source 48 is converged by a condenser lens 50 and transmitted through the reaction liquid in the reaction cuvette 46. The transmitted beam is passed through a slit 52 to be incident on a diffracting grating 54. Diffracted monochromatic light beams from the diffracting grating 54 are detected in a photodiode array 56. In each of the channels 36, 38, ... a particular item of examination is done, that is, the same reagent is poured into the reaction cuvettes 46 in the same channel. A sample, e.g., a serum, is distributed through a tube 42 and pipette 44 into the reaction cuvettes 46 in the same channels 36, 38, .... In each tube, it is mixed with a reagent so that a reaction liquid is produced. Changes in the absorbance of the reaction liquid with time are measured by each diffracting grating 54 and photodiode array 56.

In this apparatus, the absorbance is measured by the same spectrometer (i.e., by diffracting grating 54 and photodiode array 56) for each particular item, and the measurement is thus free from errors due to fluctuations of the spectrometer's detection characteristics. However, the light source 48 must be provided for each channel. Therefore, the operation and service are rather cumbersome. In addition, high power must be consumed for driving the light sources. Further, the size of the apparatus is inevitably large.

According to the invention disclosed in U.S. Pat. No. 3,697,185, while a sample such as a serum flows through a tube, a reagent is added to the sample, and the absorbance of the resultant reaction liquid is measured under temperature-controlled conditions. The measurement of absorbance is done by causing filtered beams of particular wavelengths to be incident on the reaction liquid at successively provided measuring stations.

In this apparatus, measuring stations are provided for the respective wavelengths of the absorbance measurement, so that an enlarged apparatus is again inevitable. In addition, it is probable that stray light which is incident on the detector will cause an error in the detection. Further, the precision of detection is influenced by the balance of the filter.

SUMMARY OF THE INVENTION

One object of the present invention is to provide an apparatus for absorptiometric analysis, with which the measurement of absorbance for a plurality of channels can be done by a single spectro-photometric means, so that it is possible to obtain high precision of absorbance measurement and highly reliable examination results.

Another object of the present invention is to provide an apparatus for absorptiometric analysis, which can use a single and common light source in the absorbance measurement of a plurality of channels, so that it is possible to reduce the size of the device.

A further object of this invention is to provide an apparatus for absorptiometric analysis, which is free from decomposition or like adverse reactions of the reaction liquid which is the subject of measurement.

According to the invention, an apparatus is provided for measuring the absorbance of reaction liquids contained in reaction vessels, at n measuring points for m channels, comprising:

illuminating means for emitting a beam;

means for guiding the beam from the illuminating means to the reaction liquid contained in m×n reaction vessels, at n measuring points for m channels, the illumination beam guiding means including m×n illumination beam guiding optical fibers, with every m optical fiber thereof guiding the beam from the illuminating means to each of the n measuring points;

means for guiding the transmitted beam, including m×n transmitted beam guiding optical fibers for guiding the beam transmitted through the reaction liquids in the respective m×n reaction vessels;

beam switch means including support means for supporting the beam emission ends of the transmitted beam guiding optical fibers in a circle, and in such a way that beams emitted from the beam emission ends are substantially parallel to one another, a first reflecting mirror being rotatably provided at a position of incidence of the beams from the transmitted beam guiding optical fibers, and a second reflecting mirror for reflecting the beam reflected from the first reflecting mirror in such a way that the beam reflected from the second reflecting mirror proceeds along a constant optical path;

a plurality of slit members disposed along the optical path of the beam reflected from the second reflecting mirror;

a diffraction grating for diffracting the beam having been passed through the slit members; and a photo-detector array, including a plurality of photo-detectors, for detecting diffracted monochromatic beams from the diffraction grating.

According to this invention, the measurement of the absorbance of reaction liquids for a plurality of channels at a plurality of measuring stations is done by the common diffraction grating of photo-detector array. Thus, unlike the conventional arrangement using a plurality of spectrometers, the measurement is free from errors due to fluctuations of the light-electricity conversion characteristics among different spectrometers, and complicated error correction with respect to the different spectrometers is unnecessary. In addition, the size and cost of the apparatus can be reduced.

Further, the beam emitted from the single illuminating means (i.e., from a single light source) is led through the optical fibers to the individual reaction vessels. Thus, the apparatus can be operated and serviced more easily and can consume less power compared to the conventional structure using a plurality of light sources.

Further, since light is led to and from the individual measuring stations through optical fibers, the apparatus can be further reduced in size. Furthermore, since transmitted beams from the reaction liquids for a plurality of channels and at a plurality of measuring stations are selectively led to the slit members with the rotation of the first reflecting mirror, the switching of transmitted beams to be detected by the diffraction grating and photo-diode array can be done at a high speed, so that the processing speed can be increased.

Moreover, if a light source driven for light emission by a pulse drive system, e.g., a xenon flash lamp, is used as the illuminating means, the light energy supplied per unit of time may be low, though the brightness is high, so that it is possible to avoid adverse effects of illumination on the reaction liquid. Further, with the high brightness of the illumination light, the intensity of the transmitted beam can be detected with a high degree of precision, even if the filling factor of the optical fibers is so low that light loss therein is high.

DETAILED DESCRIPTION OF THE PREFERRED EMBODIMENTS

Figure 1:
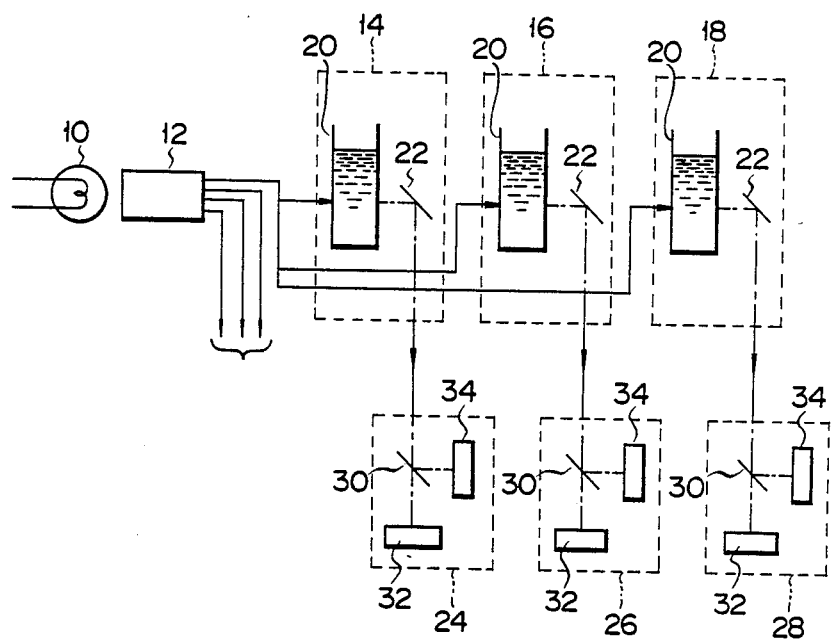
FIG. 1 is a schematic representation of a conventional apparatus for absorptiometric analysis.
Figure 2:
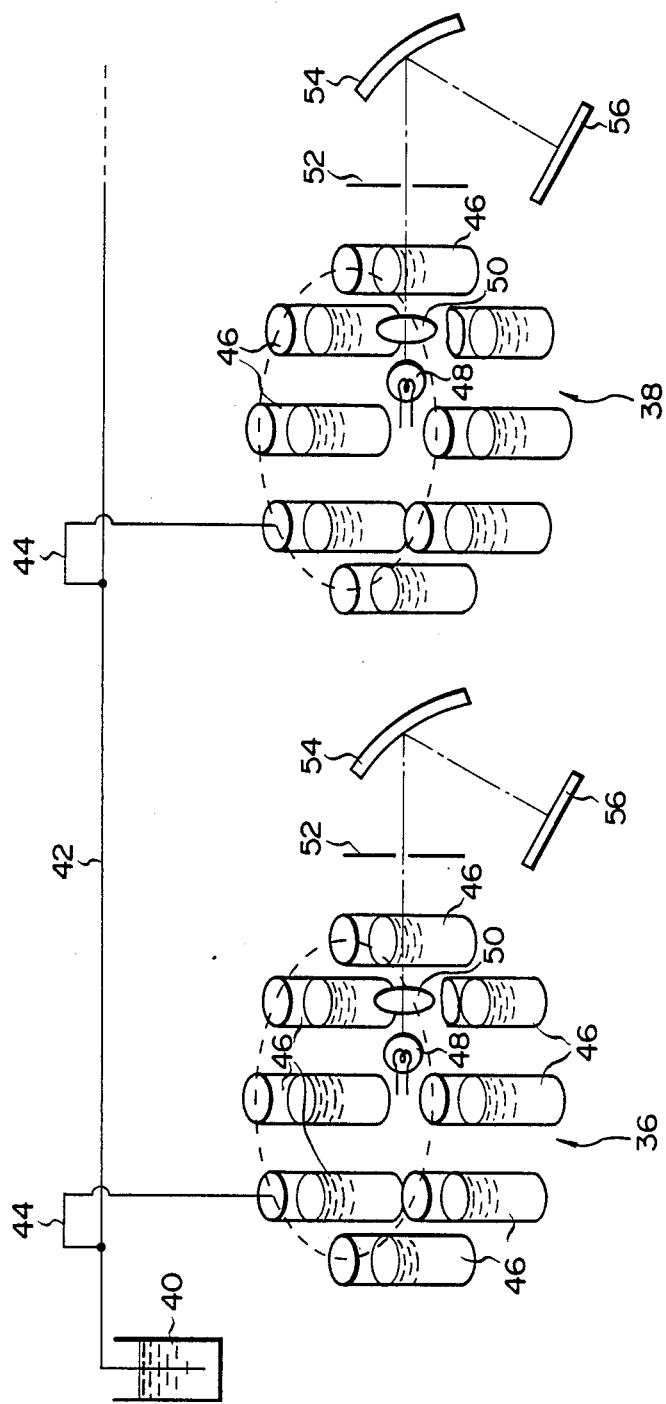
FIG. 2 is a schematic representation of another conventional apparatus for absorptiometric analysis.
Figure 3:
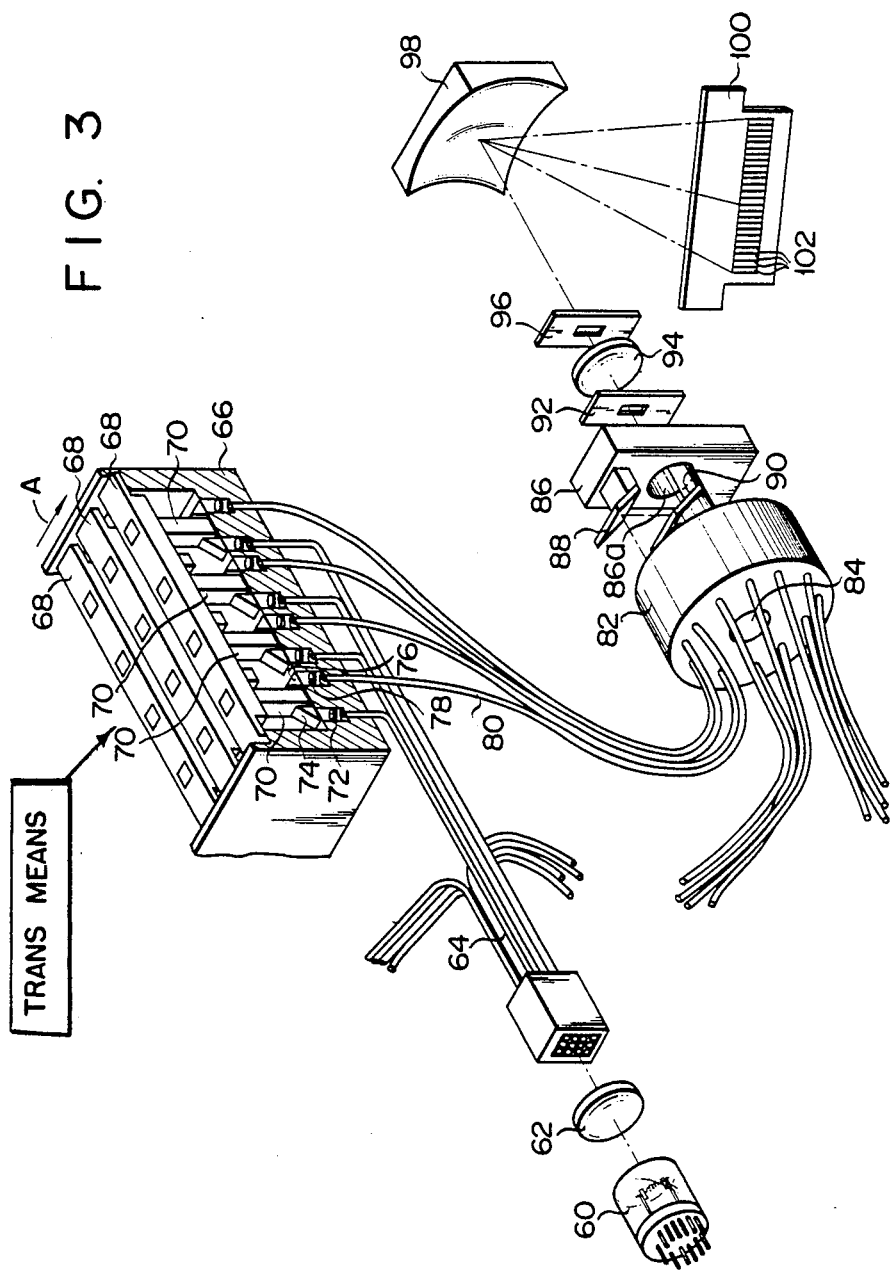
FIG. 3 is an exploded perspective view showing an embodiment of the apparatus for absorptiometric analysis according to the present invention.
Figure 4:
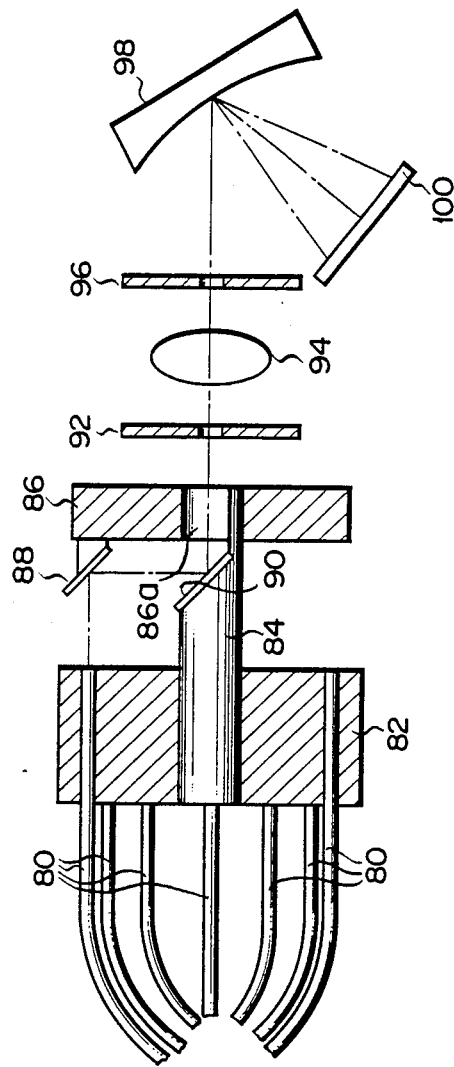
FIG. 4 is an axial sectional view showing beam switch means and a light detection system in the same embodiment.

FIGS. 3 and 4 show an embodiment of the apparatus for measuring absorbance according to the present invention. A light source 60 as shown in FIG. 3 is a xenon flashed lamp. It is driven by a pulse drive system and emits a high brightness beam as light pulses, for instance with a pulse duration of 3 μsec and at a frequency of 100 Hz. Further, it intermittently emits a beam, for instance 12 times in every 6 seconds, as will be described later in detail. The beam emitted from the light source 60 is converged by a condenser lens 62 into a parallel beam, which is incident on the beam receiving end of a bundle of optical fibers 64 for guiding the illumination beam (which are 12 in number in the illustrated example).

A plurality of cassettes 68 (only three thereof being shown), each supporting four reaction cuvettes 70 arranged in a row, are arranged in an endless line perpendicular to the row of reaction cuvettes 70 in each cassette 68. The reaction cuvettes 70 supported by the individual cassettes 68 have their lower half immersed in a constant-temperature medium, e.g., warm water, contained in a thermostatic bath 66. The constant-temperature medium is held at a predetermined reaction temperature. The cassettes 68 are fed intermittently along the endless line by transfer means 104, well known to those skilled in the art, in the direction of arrow A in FIG. 3 with supported reaction cuvettes 70 partly immersed in the medium. For instance, they are intermittently moved by transfer means 104 to a position having been occupied by the preceding cassette after they have been held stationary for 6 seconds.

Three measuring stations, for instance, are provided on the endless line at suitable positions thereon, at which positions the cassettes 68 are held stationary for the period noted above. In each measuring station, four pairs of beam path defining members 74 and 76, e.g., reflecting mirrors or prisms, are provided. The beam path defining members 74 and 76 in each pair are disposed on the opposite sides of each reaction cuvettes 70 in the longitudinal direction of the cassette 68. A condenser lens 72 having a vertical lens axis is disposed right beneath each beam path defining member 74. The emission end of each of the optical fibers 64 for guiding the illumination beam is disposed right beneath each condenser lens 72 such that its optical axis coincides with the lens axis of the condenser lens 72. A condenser lens 78 having a vertical lens axis is disposed right beneath each beam path defining member 76. The beam receiving end of each of optical fibers 80 for guiding the transmitted beam is disposed right beneath each condenser lens 78 such that its optical axis coincides with the lens axis of the condenser lens 78. The beam emitted from each optical fiber 64 is condensed by each condenser lens 72, and its path is then changed by each beam path defining member 74 to a horizontal path. The horizontal beam is transmitted through the reaction liquid in each reaction cuvettes 70. The path of the transmitted beam is diverted by each beam path defining member 76 toward each condenser lens 78, so that the beam is condensed in such a way as to be incident on each optical fiber 80.

Of the 12 optical fibers 64 for guiding the illumination beam noted above, every four optical fibers are led to each of the three measuring stations. In each measuring station, the four optical fibers 64 are led to their respective reaction cuvettes 70. The optical fibers 80 for guiding the transmitted beam led out from the reaction cuvettes 70 at the measuring positions constitute a bundle of optical fibers. They are 12 in number, and four of them are led out from the respective reaction cuvettes 70 in each measuring station.

The beam emission ends of the 12 optical fibers 80 are supported by a support member 82 at positions thereof which fall on a circle. The support member 82 is secured to the frame of the apparatus. A shaft 84 rotatably penetrates the center of the support member 82 and extends substantially at right angles to the plane of the support member 82. The beam emission ends of the 12 optical fibers 80 are uniformly spaced on the support member 82 along a circle with the center thereof concentric with the axis of the shaft 84. They are secured to the support member 82 such that they extend parallel to the axis of the shaft 84. The beam receiving end and beam emission end of the optical fibers 64 and the beam receiving end of the optical fibers 80 are all circular in sectional shape. The beam emission end of the optical fibers 80, however, is elongated in sectional shape like a slit. The beam emission ends of the individual optical fibers 80 are secured to the support member 82, in such a way that they extend in the same direction.

The shaft 84 projects from the side of the support member 82, opposite the side on which the beam emission ends of the optical fibers 80 are secured. A rotor 86 is secured to the free end of the projecting portion of the shaft 84. It carries a reflecting mirror 88 mounted on its side facing the support member 82 and at a position which is adapted to be brought into alignment with the beam emission end of each optical fiber 80. The shaft 84 carries a reflecting mirror 90 facing the reflecting mirror 88. The shaft 84 also has a notch formed in its portion on the side of the reflecting mirror 90 nearer the rotor 86 and also sectionally on the side nearer the reflecting mirror 88. The rotor 86 has a see-through hole 86a corresponding in position to the notch of the shaft 84. The beam emitted from the beam emission end of the optical fiber 80 aligned to the reflecting mirror proceeds along a path as shown by a dot-and-bar line. More particularly, it first proceeds along a path parallel to the axis of the shaft 84 and is reflected by the reflecting mirror 88 to be incident on the reflecting mirror 90.

The beam reflected by the reflecting mirror 90 proceeds along a path substantially coincided with the axis of the shaft 84, through the see-through hole 86a of the rotor 86.

A pair of slit members 92, 96 is disposed on the path of the beam from the rotor 86 (i.e., on the axis of the shaft 84). A condenser lens 94 is further disposed on the beam path noted above between the slit members 92 and 96. The slit members 92 and 96 have respective slits extending in the direction of the elongated beam emission ends of the optical fibers 80, the section of the emission ends having a shape corresponding to the slits of the slit members 92 and 96.

The beam having passed through the slit member 96 is incident on and is diffracted by a diffraction grating 98. The diffracted beam is incident on a photodiode array 100 consisting of a plurality of photodiodes 102 arranged in a row. The intensity of the beam for each particular wavelength is detected by each photodiode 102. More specifically, the photodiodes 102 convert the incident beam into electric signals, which are transferred to a calculating unit (not shown). The calculating unit calculates the absorbance of the reaction liquid according to the results of detection of the intensity of the transmitted beam provided from the photodiode array 100.

The operation of the apparatus having the above construction may be described as follows. A sample, e.g., a serum of a patient, is distributed into the four reaction cuvettes 70 supported by each cassette 68. Predetermined reagents for different examination items, i.e., GOT, GPT, α-GPT and amilase are charged into the respective reaction cuvettes 70. The individual cassettes 68 with the reaction cuvettes 70 containing respective reaction liquids (i.e., mixtures of sample and reagent) are intermittently moved by transfer means 104 in the direction of arrow A in FIG. 3, along the endless line with the reaction liquids held at a constant temperature by the constant-temperature medium in the thermostatic bath 66. They are held stationary, e.g., for 6 seconds, at the first to third measuring stations. After each cassette 68 is moved from each measuring station, the succeeding cassette 68 is moved to that station by transfer means 104.

While the cassettes 68 are stationary, the light source 60, which is a xenon flashed lamp, is driven to emit beams intermittently, 12 times. The beam emission is caused by a pulse drive system with a flashing period of approximately 3 μsecond and a flashing frequency of 100 Hz. One beam emission period is 0.2 seconds. Thus, even if the amplitude of the pulse and, hence, the brightness of the beam, is high, the integral of the amount of beam emitted per unit time or the total energy (in Watts) of beam transmitted through the reaction liquid per unit time is extremely low compared to the prior art case using the halogen lamp. For this reason, there is no possibility of decomposition or other undesired reactions of a reaction liquid, even if the xenon flashed lamp with about 1,000 times the brightness of the halogen lamp is used. Also, optical fibers of a low filling factor may be used as the optical fibers 64 and 80 to obtain the measurement of absorbance without being adversely influenced by the loss of light because of the high brightness of the beam. The inventor conducted experiments about the decomposition of bilirubin by illumination of flashlight from the xenon flashed lamp, and it was confirmed that the decomposition that results is very little compared to the case of continuous illumination using the halogen lamp. The same effects may be obtained by using a mercury flashed lamp, a pulse laser, etc., in lieu of the xenon flashed lamp serving as the light source 60. Further, the same effects may be obtained by using an illuminating means which provides a beam from a halogen lamp, as a non-continuous beam; by means of chopping, instead of the pulse drive system light source.

The beam emitted from the light source 60 is coupled, through the condenser lens 62, to the beam receiving ends of the optical fibers 64. Through these optical fibers 64, the beam is led to the reaction vessels 70 in the first to third measuring stations. More specifically, the beam emitted from the beam emission end of each optical fiber 64 is coupled through the associated condenser lens 72 and beam path defining member 74 and transmitted through the reaction liquid in the reaction cuvette 70. The transmitted beam is coupled through the associated beam path defining member 76 and condenser lens 78 to be incident on the beam receiving end of the corresponding optical fiber 80. The beam coupled to the optical fibers 80 is emitted from the beam emission ends thereof supported by the support member 82. During each stationary period of the cassettes 68, the transmitted beam is emitted 12 times from the beam emission ends of the 12 optical fibers 80.

While the transmitted beam is being emitted from the bundle of optical fibers 80 for the first period, the rotor 86 is held at a position at which the beam emission end of the first optical fiber 80 in the bundle is aligned to the reflecting mirror 88. When the emission of the transmitted beam for the first period is over, the rotor 86 is rotated to a next stationary position, at which the beam emission end of the second optical fiber 80 adjacent to the first optical fiber is aligned to the reflecting mirror 88. The rotor 86 is held stationary at this position during the emission of the transmitted beam for the second period. When the second period of transmitted beam emission is over, the rotor 86 is moved again and is brought to a position, at which the third optical fiber 80 adjacent to the second is aligned to the reflecting mirror 88. This sequence of operation of the rotor 86 is caused 12 times successively while the cassettes 68 are held stationary. While the rotor 86 is intermittently rotated to complete one rotation, beams transmitted through the reaction liquids in the 12 reaction vessels at the first to third measuring stations are successively caused to pass through the slit member 92, condenser lens 94 and slit member 96. It is to be understood that the rotor 86 serves as beam switch means for independently and successively supplying beam transmitted through the reaction liquids in the individual reaction cuvettes 70 through the slit member 92, condenser lens 94 and slit member 96. Since the path of the transmitted beam is regulated by the pair of reflecting mirrors 88, 90, the transmitted beam emitted from each optical fiber 80 can be supplied to the slit member 92 without substantial loss.

The transmitted beam, having been passed through slit member 92, the condenser lens 94 and slit member 96, is incident on the diffraction grating 98. The diffracted beam from the diffraction grating 98 is detected by the photo-detectors 102 of the photo-detector array 100 for individual predetermined wavelengths. The slit members 92, 96 are provided for increasing the directivity of the transmitted beam. While with a single slit, the directivity of transmitted light is not significantly increased, it can be substantially increased by providing a pair of slits. Meanwhile, the beam emission end of the optical fibers 80 has an elongate shape corresponding to the shape of the slit of the slit members 92 and 96. That is, a beam having an elongate sectional shape is emitted from the beam emission end of each optical fiber 80. Thus, the proportion of the transmitted beam blocked by the slit member 92 is very low compared to the case where an ordinary beam having a circular sectional profile is blocked by the slit member 92. This means that the light energy of the transmitted beam emitted from the beam emission end having the elongate shape similar to the shape of the slit is blocked only slightly by the slit members 92 and 96, so that it can be effectively supplied to the photo-detectors 102.

Data on the intensity of the transmitted beam detected by the photo-detectors 102 is stored in a memory of the calculating unit. While the cassettes 68 are held stationary, the intensity of the transmitted beam from the reaction liquids in the 12 reaction cuvettes 70 is obtained for the individual predetermined frequencies. This data are stored in the memory. They are obtained and stored every time the cassettes 68 are moved to the next position.

After the intensity of the transmitted beam with respect to each cassette has been measured for all of the measuring stations, the calculating unit reads out data on the intensity of the transmitted beam which data is obtained with respect to a particular reaction liquid for the first to third measuring stations and is selected from among data stored in the memory, thereby calculating the absorbance. At this time, the absorbance is usually obtained on the basis of a commonly termed two-wavelength measurement, to eliminate background noise. More specifically, the difference between the absorbances with respect to two wavelengths, i.e., a main wavelength and an auxiliary wavelength, is obtained from the data obtained at each measuring station. This difference in the absorbance is multiplied by a preliminarily obtained constant for conversion to the absorbance with respect to the main wavelength. In the above embodiment, the wavelength accuracy is high, since the transmitted beam is incident on the diffraction grating 98 after it has been passed through the pair of slit members 92 and 96. Thus, the two-wavelength measurement can be obtained with a high degree of accuracy, without a deviation in the pattern relating to the wavelength, or absorbance with respect to the wavelength.

The absorbance obtained for each reaction liquid, in the above-described manner, is plotted against time, until the reaction cuvette is brought to the first to third measuring stations, after addition of the reagent to the sample. Changes in the absorbance, i.e., the reaction degree, with time thus can be obtained. Whether the pertinent patient is normal or not with respect to the given reagent item is judged from the changes in the reaction degree with time.

It is to be further understood by those skilled in the art that the foregoing description is for the sole purpose of illustrating the preferred embodiment of this invention, and that various changes and modifications may be made to the invention, without departing from its scope and spirit. For example, the number of channels and number of measuring stations are not limited to 4 and 3, respectively, as in the above embodiment, but may be suitably set, according to the examination items and other factors. Further, three or more slit members may be provided, instead of a pair of slit members, between the rotor 86 and diffraction grating 98. Still further, it is possible to provide the beam switch means comprising the support member 82, shaft 84, rotor 86 and reflecting mirrors 88, 90, between the condenser lens 62 and the bundle of optical fibers 64. In this case, the beam from the light source 60 is successively distributed to the 12 optical fibers, with the rotation of the rotor 86. Thus, no beam is supplied to the reaction liquid, with respect to which the measurement of absorbance is not made. Thus, the influence of the transmitted beam on the reaction liquid can be further reduced. Finally, while the above embodiment has used condenser lenses 72, 78 and beam path defining members 74, 76 in guiding beams to and from the reaction liquids, it is also possible to arrange the beam emission ends of the optical fibers 64 and the light receiving ends of the optical fibers 80 in such a way that they directly face the reaction cuvettes 70, so that the beam from the optical fibers 64 is directly incident on the reaction liquids and the transmitted beam is directly incident on the optical fibers 80.

What is claimed is:

1. An apparatus for measuring absorbances of samples contained in reaction vessels, comprising:

illuminating means for emitting light beams;

measuring means for measuring the intensity of the light beams transmitted through the samples contained in the vessels;

transfer means for transferring reaction vessels successively forwarded to predetermined measuring points on a reaction line;

guiding means having stationary optical fibers, each with a beam-receiving end and a beam-emitting end, for guiding through a first portion of said stationary fibers light beams emitted from the illuminating means to the samples contained in the respective vessels staying at the measuring points, and for guiding through a second portion of said stationary fibers the light beams transmitted from the respective samples to the measuring means;

switching means for selecting one transmitted light beam through the reaction vessel staying at one measuring point, and directing the selected beam to the measuring means, said switching means including;

(a) a holder for holding the optical fibers, the beam-emitting ends of which are arranged so that the light beams passing through the optical fibers are emitted substantially simultaneously from the respective beam-emitting ends of the optical fibers;

(b) a first mirror for reflecting one light beam transmitted from the corresponding fiber;

(c) a rotating member for rotating the first mirror to align the same with the beam-emitting ends of said optical fibers one after another, so that said first mirror reflects the light beams from the corresponding fibers, the first reflecting mirror scanning the beam-emitting ends of all optical fibers held by the holder, every time the first mirror rotates when the vessels stay at the measuring points; and (d) a second mirror for reflecting said light beam reflected from said first mirror and passing it through a common light path to said measuring means, regardless of the position of the optical fiber aligned with the first mirror;

a plurality of slit members disposed along the common light path; and a diffraction grating, disposed along the common light path downstream of said slit members, for diffracting the beam that has passed through said slit members.

2. The apparatus according to claim 1, wherein the illuminating means includes a light source, which is driven by a pulse drive system to emit said light beams, such as any one of a xenon flashed lamp, a mercury flashed lamp and a pulse laser.

3. The apparatus according to claim 2, wherein said guiding means further includes beam path defining members, each of which is used for directing the beam emitted from each of the illumination beam guiding optical fibers to the samples in each of the reaction vessels; and condenser lenses, each of which is interposed between each of the beam path defining members and the beam emission end of each of the illumination beam guiding optical fibers.

4. The apparatus according to claim 3, wherein said guiding means further includes transmitted beam path defining members, each of which is used for directing the beam transmitted through the samples in each of the reaction vessels to the beam receiving end of each of the transmitted beam guiding optical fibers; and condenser lenses, each of which is interposed between each of the transmitted beam path defining members and the beam receiving end of each of the transmitted beam guiding optical fibers.

5. The apparatus according to claim 2, wherein the switching means further includes a shaft having an axis coaxial with the center of the circle of the holder and extending parallel to the beams emitted from the transmitted beam guiding optical fibers, the shaft being rotatably supported in the holder, and a rotor being secured to the shaft; and, wherein, the following conditions apply; the first reflecting mirror is secured to the rotor; the second reflecting mirror is secured to the shaft; the rotor has a see-through hole, through which the path of the beam reflected by the second reflecting mirror extends; and the transmitted beam emitted from each of the transmitted beam guiding optical fibers is reflected by the first and second reflecting mirrors and proceeds along a substantially constant beam path, through the see-through hole, while the rotor completes one rotation.

6. The apparatus according to claim 5, wherein the beam emission end of each of the transmitted beam guiding optical fibers has an elongate sectional shape, and the elongate beam emission ends of all of the transmitted beam guiding optical fibers extend in the same direction.

7. The apparatus according to claim 6, wherein said slit members are disposed between the rotor and diffraction grating, a condenser lens being interposed between individual ones of said slit members.

* * * * *